United States Patent [19]
Akkara et al.

[11] Patent Number: 5,846,753
[45] Date of Patent: Dec. 8, 1998

[54] CHEMILUMINESCENCE-BASED METHOD FOR RAPID AND SENSITIVE IN-SITU DETECTION OF ORGANOPHOSPHORUS COMPOUNDS AND METAL IONS

[75] Inventors: Joseph A. Akkara, Holliston; David L. Kaplan, Stow; Madhu S. R. Ayyagari, Brighton; Kenneth A. Marx, Francestown; Sanjay Kamtekar; Rajiv Pande, both of Lowell; Sukant K. Tripathy, Acton; Jayant Kumar, Westford, all of Mass.

[73] Assignee: The United States of America as represented by the Secretary of the Army, Washington, D.C.

[21] Appl. No.: 445,565

[22] Filed: May 30, 1995

[51] Int. Cl.$^6$ .......................... C07D 305/14; C12Q 1/42; C12Q 1/44

[52] U.S. Cl. .......................... 435/18; 549/332; 549/222; 435/19; 435/21

[58] Field of Search .............................. 435/21, 18, 19; 549/222, 332

[56] References Cited

U.S. PATENT DOCUMENTS

| | | | |
|---|---|---|---|
| 3,582,209 | 6/1971 | LaRosa et al. | 356/51 |
| 3,910,763 | 10/1975 | Poziomek et al. | 23/232 R |
| 4,385,113 | 5/1983 | Chappelle et al. | 435/8 |
| 5,013,827 | 5/1991 | Schaap | 536/17.3 |
| 5,089,390 | 2/1992 | Davalian et al. | 435/7.93 |
| 5,112,960 | 5/1992 | Bronstein et al. | 536/18.1 |
| 5,145,772 | 9/1992 | Voyta et al. | 435/4 |
| 5,169,554 | 12/1992 | Akkara et al. | 252/174.12 |
| 5,223,402 | 6/1993 | Abbas et al. | 435/18 |
| 5,270,164 | 12/1993 | Anderson et al. | 435/6 |
| 5,330,900 | 7/1994 | Bronstein et al. | 435/6 |
| 5,393,469 | 2/1995 | Akhavan-Tafti | 252/700 |

OTHER PUBLICATIONS

Ayyagari et al., Biotechnol. Prog., 11, 699–703 Nov. 1995.
Ayyagari et al., Biotech. Bioengineering, 45, 116–121 Jan. 1995.
Kricka, Clin. Chem., 39(9), 1472–81 Sep. 1991.
Martinez, R.C., Gonzalo, E.R., Moran, M.J., and Mendez, J.H. (1992) *J. Chromatography*, 607, 37–45.
Sanchez, F.G., Lopez, M.H., and Pareja, A.G. (1991) Anal. Chim. *Acta*, 255, 311–316.
Bier, F.F., Stocklein, W., Bocher, M., Bilitewski, U., and Schmid, R.D. (1992) *Sensors and Actuators B*, 7, 509–512.
Palleschi, G., Bernabie, M., Cremisini, C., and Mascini, M. (1992) *Sensors and Actuators B*, 7, 513–517.
Trettnak, W., Reininger, F., Zintrel, E., and Wolfbeis, O.S. (1993), *Sensors and Actuators B*, 11, 87–93.
Thompson, R.B., and Jones, E.R. (1993) *Anal. Chem.*, 65, 730.
Blair, T.L., Yang, S., Smith–Palmer, T., and Bachas, L.G. (1994) *Anal. Chem.*, 66, 300.
Burguera, J.L., Burguera, M. and Townshend, A. (1981) *Anal. Chim. Acta*, 127 199.
Coleman, J.E., *Annaual Rev. Biophys. Biomol. Struct.*, 21, 441. (1992).
Townshend, A., and Vaughan, A., *Talanta*, 16, 929, (1969).
Guilbault, G., Sadar, M.H., and Zimmer, M. (1969) *Anal. Chim. Acta*, 44, 361.
Townshend, A., and Vaughan, A. (1970) *Anal. Chim. Acta*, 49 366.
Poznansky, M.J. (1988) *Methods Enzymol.*, 137, 566.

*Primary Examiner*—Johann Richter
*Assistant Examiner*—Laura R. Cross Lutz
*Attorney, Agent, or Firm*—Vincent J. Ranucci

[57] ABSTRACT

A method of detecting the presence of a substance being monitored in a medium, selected from the group of substances including organophosphorus compounds and the metal ions Zn, Be and Bi, including the steps of: providing a 1,2-dioxetane phenyl phosphate compound; providing a phosphatase that catalytically degrades the 1,2-dioxetane phenyl phosphate compound to produce light, the catalytic activity of the phosphatase toward 1,2-dioxetane phenyl phosphate compound being altered by the substance being monitored; exposing the 1,2-dioxetane phenyl phosphate compound and the phosphatase together to a medium which may contain the substance being monitored; detecting light produced after the exposing step; and determining, from the detected light, the presence and concentration in the medium of the substance being monitored.

27 Claims, 18 Drawing Sheets

○ Alkaline Phosphatase

▭ - CSPD      ▭ ▭ Dissociated CSPD

∽ - Glutaraldehyde spacer

CHEMILUMINESCENCE-BASED METHOD FOR RAPID AND SENSITIVE IN-SITU DETECTION OF ORGANOPHOSPHORUS COMPOUNDS AND METAL IONS

FIELD OF INVENTION

This invention relates to a method of detecting organophosphorus compounds, and metal ions, using chemiluminescence-based chemistry.

BACKGROUND OF INVENTION

A number of organophosphorus compounds are used as pesticides and nerve agents. Detection and quantification of these highly toxic compounds by remote sensors at very low levels in the surrounding environment are critical during their production, storage, transportation, and decontamination processes. Organophosphorus-based pesticides, including paraoxon, parathion and diazinon are widely used in agriculture industry and the resultant environmental pollution is well documented. Because of their toxicity and relatively high solubility in water, organophosphorus-based pesticides pose a clear threat to drinking water and aquatic life. It is therefore necessary to monitor the levels of these materials in industrial waste waters, agricultural runoffs, and other environments to determine compliance with federal and state regulations and other safety guidelines, as well as efficiency of wastewater treatments.

It is in the interest of the Department of Defense as well as the EPA that these organophosphorus compounds be detected in the environment and quantified. In response to this need, a variety of techniques have been studied based on physical, chemical and biological approaches to detect and quantify organophosphorus compounds. Although all these techniques have some degree of sensitivity, they lack simplicity, rapid detection and portability. It is therefore necessary to develop a detection system that addresses these features.

In addition to the organophosphorus compounds, detection of the presence of heavy metal ions in trace quantities in waste water or drinking water is essential from a health and environmental safety viewpoint. A sensitive, reliable and rapid method to detect and quantify such metal ions as Zn(II), Be and Bi is much needed for on-site analysis of the quality of the water. Although the currently existing techniques are sensitive, they suffer from lack of simplicity, portability and speed of response.

SUMMARY OF THE INVENTION

It is therefore an object of this invention to provide a chemiluminescence-based method for detection of organophosphorus compounds in parts per billion (ppb) levels.

It is a further object of this invention to provide such a method which can also detect metal ions in parts per billion (ppb) levels.

It is a further object of this invention to provide such a method which may be accomplished in situ.

It is a further object of this invention to provide such a method which is two orders of magnitude faster than other similar methods.

It is a further object of this invention to provide such a method which does not require an external light source.

It is a further object of this invention to provide such a method which can be incorporated into a fiber-optic based sensor for remote detection.

This invention features methods of detecting the presence of a substance being monitored. Most basically, the method uses inhibition of chemiluminescence signals generated by enzyme action to detect and apoenzyme quantify organophosphorus compounds and metal ions. Regeneration of apoenzyme activity is also used to detect and quantify zinc in ppb levels.

1,2-dioxetane phenyl phosphate compounds are catalytically decomposed by phosphatase enzymes. The decomposition emits light. The enzyme activity toward the 1,2-dioxetanes is inhibited by the presence of organophosphorus compounds and metals such as zinc, bismuth and beryllium. Thus, the presence of such inhibiting compounds leads to the generation of a weaker chemiluminescence signal than if the compounds are not present. The chemiluminescence signal intensity from the decomposition of the 1,2-dioxetane phenyl phosphate compounds is thus inversely proportional to the concentration of the inhibitor species being detected. Inhibitor concentrations can be quantified by comparing chemiluminescence signal strength to standard curves developed with known concentrations of the inhibitor compounds.

Zinc detection and quantification by activity regeneration involves first preparing an apoenzyme from the native enzyme by removing metal ions from the enzyme structure. The apoenzyme now lacks the catalytic activity that can be regenerated in the presence of externally provided zinc ions. Since the regenerated activity is directly proportional to the amount of zinc, the metal ion can be quantified by measuring the increase in apoenzyme activity.

The phosphatase enzymes having the desired activity include alkaline phosphatase, acid phosphates, acetylcholine esterase, phosphodiesterase, phosphotriesterase, and any enzyme that catalyzes the hydrolysis of organophosphorus compounds. The 1,2-dioxetane is preferably chloro 3-(4-methoxy spiro [1,2-dioxetane-3-2'-trichloro-[3.3.1.1]-decan]-4-yl) phenyl phosphate (CSPD). The detectable inhibitor compounds include organophosphorus compounds such as nerve agents including Soman, Sarin, Tabun and VX, as well as pesticides such as malathion, methyl parathion, parathion, paraoxon and diazinon. The formulae for these substances are as follows:

$$\begin{array}{c} R3 \\ | \\ R2-P=X \\ | \\ R1 \end{array}$$

| Name | X | R1 | R2 | R3 |
|---|---|---|---|---|
| Pesticides | | | | |
| Malathion | S | $OCH_3$ | $OCH_3$ | $S-CH(CH_2COOC_2H_5)COOC_2H_5$ |
| Methyl parathion | S | $OCH_3$ | $OCH_3$ | $O-Phe-NO_2$ |
| Parathion | S | $OC_2H_5$ | $OC_2H_5$ | $O-Phe-NO_2$ |
| Paraoxon | O | $OC_2H_5$ | $OC_2H_5$ | $O-Phe-NO_2$ |
| Diazinon | S | $OC_2H_5$ | $OC_2H_5$ | O-Pyrimydyl-2isopropyl,4-methyl |
| Nerve Agents | | | | |
| Soman | O | $CH_3$ | F | $O-CH(CH_3)C(CH_3)3$ |
| Sarin | O | $CH_3$ | F | $O-CH(CH_3)2$ |
| Tabun | O | $N(CH_3)_2$ | CN | $O-C_2H_5$ |
| VX | O | $CH_3$ | $OC_2H_5$ | $S-CH_2-CH_2-N(C_3H_7)_2$ |

The methodologies may be practiced by immobilizing the enzyme on a surface. For remote detection, the enzyme may be immobilized on a fiber-optic surface which can then be used to carry the light to a remote light detector. The immobilization may be accomplished by binding the enzyme to a glass surface as follows. A biotinylated copolymer can be adsorbed on a silanized glass surface through hydrophobic interactions. The enzyme may then be conjugated to streptavidin, which binds to the polymer via the biotin-streptavidin interaction. Another enzyme binding scheme involves immobilizing the enzyme onto a silanized glass surface using glutaraldehyde cross linking.

BRIEF DESCRIPTION OF THE DRAWINGS

Other objects, features and advantages will occur to those skilled in the art from the following description of preferred embodiments and the accompanying drawings, in which.

DESCRIPTION OF THE PREFERRED EMBODIMENTS

Figure 1:
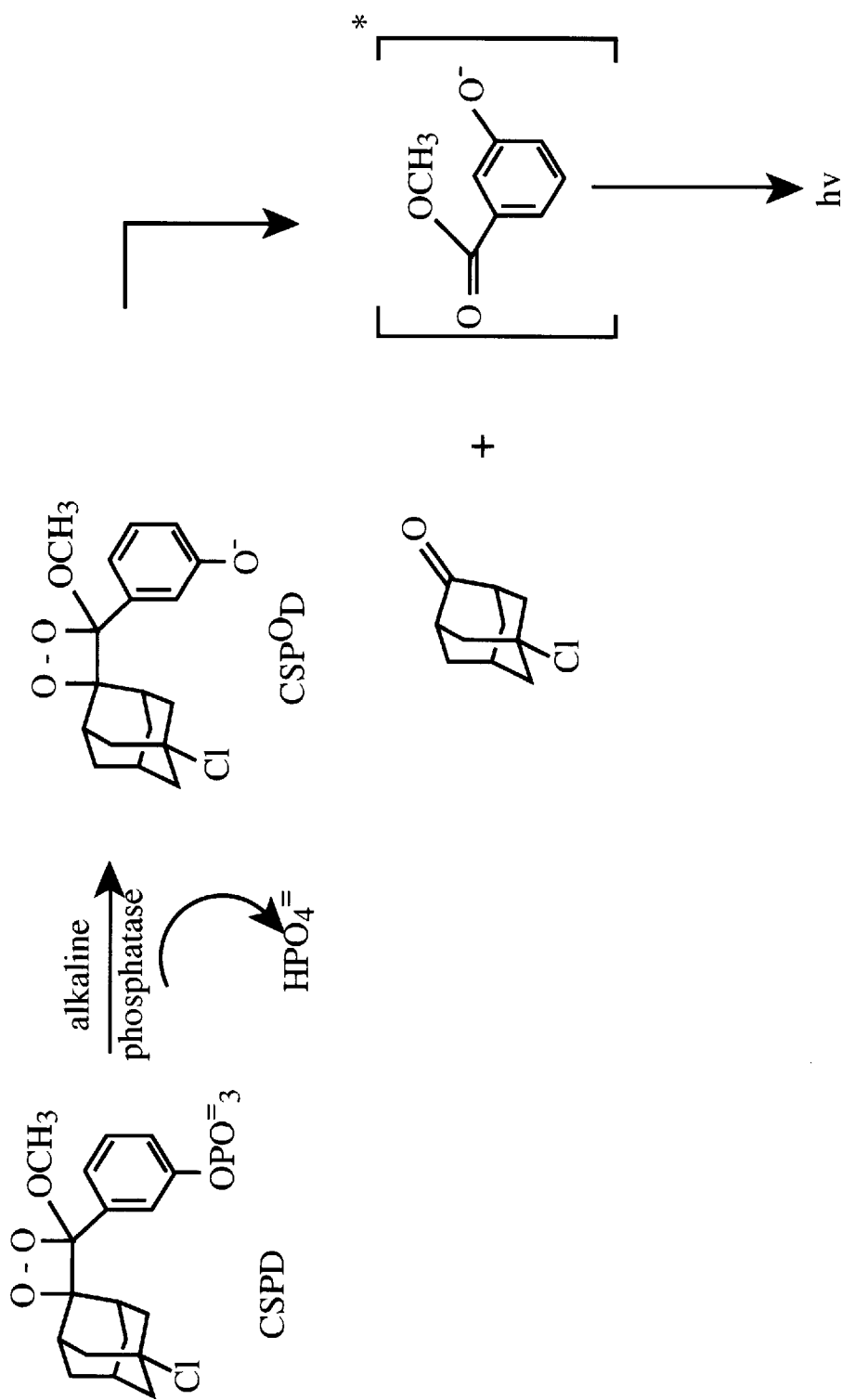
FIG. 1 depicts alkaline phosphatase catalyzed hydrolysis of CSPD.

It has been found that the catalytic dephosphorylation of 1,2-dioxetane phenyl phosphate compounds produces light. The general scheme of this reaction is depicted in FIG. 1 for CSPD as the 1,2-dioxetane, and alkaline phosphatase as the enzyme. Dephosphorylation produces an unstable phenolate anion with a weak O—O bond. This anion decomposes and emits light. The half-life of the anion varies from a few minutes to a few hours depending on its surrounding environment.

As is explained in more detail below, there are a number of compounds which bind with the phosphatase enzyme. When such substances are present, there is less active enzyme available for the reaction of FIG. 1. Thus, the presence of these substances decreases the amount of light produced in the catalytic degradation of the 1,2-dioxetane phenyl phosphate compound. Thus, if the degeneration reaction is carried out in a medium which may include such a competitive enzyme-binding compound (an inhibitor), by monitoring the strength of the chemiluminescence signal, one may determine the presence of, and the concentration of, the inhibitor compound.

Figure 2:
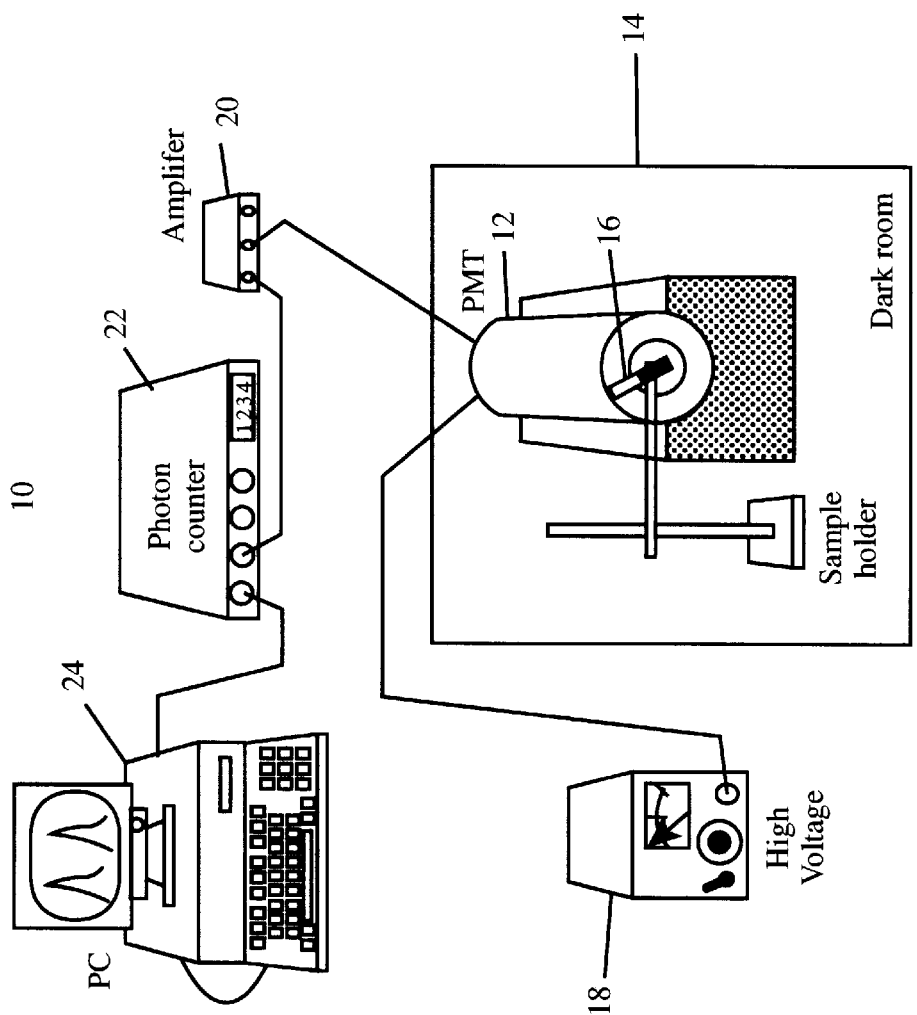
FIG. 2 is a schematic diagram of an experimental set-up for practicing the methods of this invention.

The in situ generation of light in the reaction mixture is easily detected and processed using an experimental optical setup like the one shown in FIG. 2. Experimental apparatus 10 includes photomultiplier tube 12 which is kept in dark box 14. A test tube with the necessary reaction mixture 16 is held in front of tube 12, which is supplied with high voltage from source 18. The signal from tube 12 is amplified by amplifier 20 and passed to photon counter 22, which determines the number of detected photons and passes the signal to personal computer 24 for analysis/display as desired. Thus, there is no need for an external excitation light source as is required in the case of florescence-based methodologies.

An aqueous preparation of streptavidin-conjugated alkaline phosphatase was supplied as part of Southern-Light™ Chemiluminescent Detection System by Tropix, Inc., (Bedford, Mass.). Diethylamine (DEA) and chloro 3-(4-methoxy spiro [1,2-dioxetane-3-2'-trichloro-[3.3.1.1]-decan]-4-yl) phenyl phosphate (CSPD) were also a part of this system. CSPD was available as a 25 mM aqueous solution. Sapphire™, a luminescence amplifying material (referred to as an enhancer), was also supplied by Tropix, Inc. Magnesium chloride was purchased from Fisher Scientific (Fair Lawn, N.J.). Paraoxon was supplied by Sigma Chemicals Company (St. Louis, Mo.) and malathion, methyl parathion and diazinon were purchased from PolyScience (Nile, Ill.). Deionized and distilled water was used in all preparations.

The assay buffer (0.1M DEA, 1 mM $MgCl_2$, pH 10) was prepared once every week, as recommended. The pH was adjusted with 0.1M HCl. Stock solutions of pesticides were prepared just before the experimentation, and necessary dilutions were carried out with assay buffer. CSPD stock solution was prepared by first making a 10% solution of enhancer in DEA buffer. The 25 mM CSPD solution was diluted with this solution to the extent necessary. The resultant solution was stable at room temperature for weeks. The enzyme stock solution (0.5 nM) was always freshly prepared just before the reaction. The stock solutions were stored at 4° C. until the time the reaction mixture was to be prepared. A typical reaction mixture was prepared by first adding predetermined volumes of substrate and buffer or pesticide solutions in a glass test tube. After bringing the mixture to room temperature, the reaction was initiated by adding a known volume of enzyme solution. Wherever required, buffer was used to make up the volumes. The composition of the final reaction mixture was arrived at after extensive experimentation to minimize the amounts of enzyme and CSPD and maximize the signal to noise ratio.

A photomultiplier tube (PMT), a photon counter, an amplifier and a personal computer were used to collect and process the data. FIG. 2 illustrates the schematic of this simple experimental set-up. A test tube, containing the reaction mixture, was fixed to a stand in front of the PMT. It was held in a position with the help of markers. The assembly was placed in a dark box, and the PMT was connected to a photon counter via an amplifier located in an ante-room. A solitary test tube was used in a given set of reactions with a given pesticide to eliminate the effect of tube geometry on signal intensity. Less than ten seconds elapsed between the initiation of the reaction and the start of data acquisition. The photon counter was set up to count photons detected during succeeding one second intervals. The raw data is therefore a plot of the first derivative of photon counts versus time. Hence, the first few points were integrated with time, and a counts-versus-time plot was generated. Initial velocities of the reaction were computed from the slopes calculated on the basis of the first twenty data points collected in as many seconds.

The reaction mixtures were always prepared with 0.1M DEA (pH 10) buffer containing 10% enhancer. The amounts of other components were indicated wherever needed.

Figure 3:
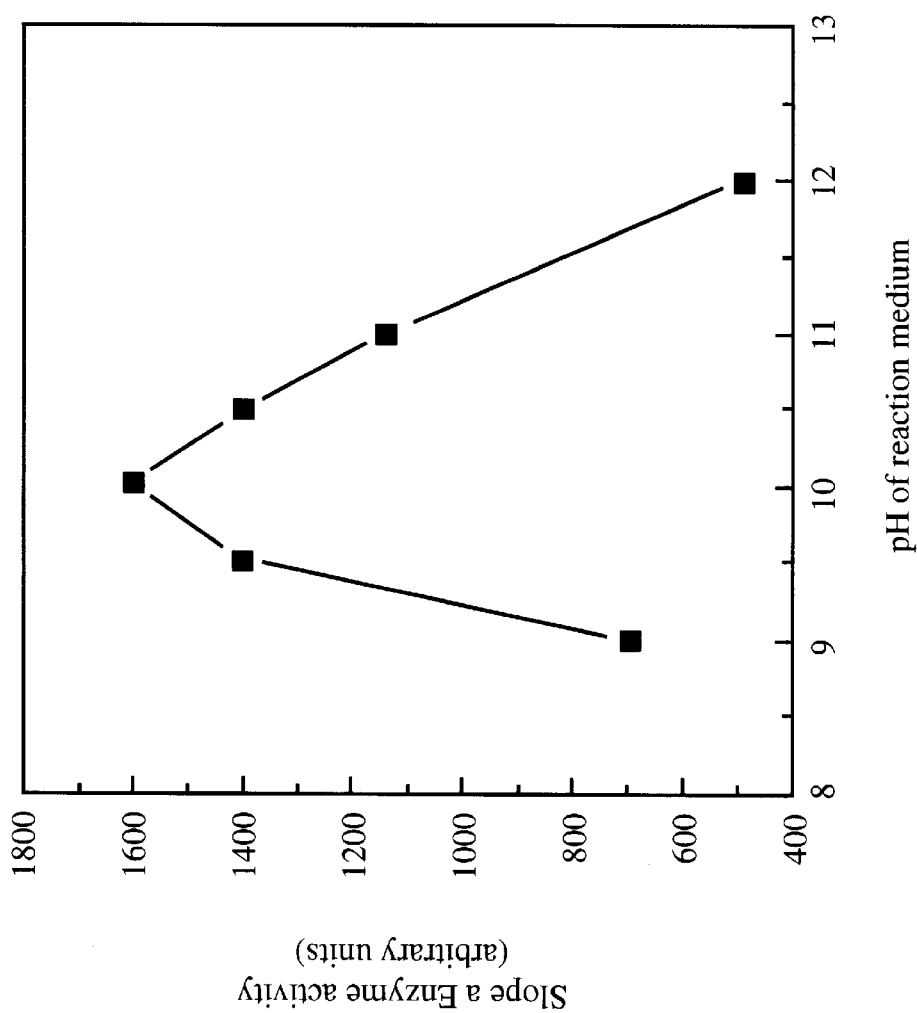
FIG. 3 is a graph of the dependence of alkaline phosphatase activity on pH.

Alkaline phosphatase is catalytically active at relatively high pH values. FIG. 3 shows the dependence of the enzyme activity, expressed in terms of chemiluminescence signal strength, on pH of the reaction mixture. The enzyme is most active at pH 10, and accordingly all reactions were conducted at that value in 0.1M DEA buffer. The following text discusses the results from the enzyme kinetics studies and the detection and quantification of organophosphorus (OP) -based pesticides. OP-based inhibitors may bind irreversibly in the active site of the enzyme, or in allosteric fashion to influence the active site. Any compound that impacts the active site or the enzyme activity in the allosteric manner can be detected based on inhibition of enzyme activity.

The hydrolysis of CSPD, catalyzed by alkaline phosphatase, is shown in FIG. 1. The amount of light generated in this reaction is proportional to the amount of product generated. Thus, the rate of light generation is proportional to the rate of product formation which is the initial velocity, v, of the reaction.

Figure 4:
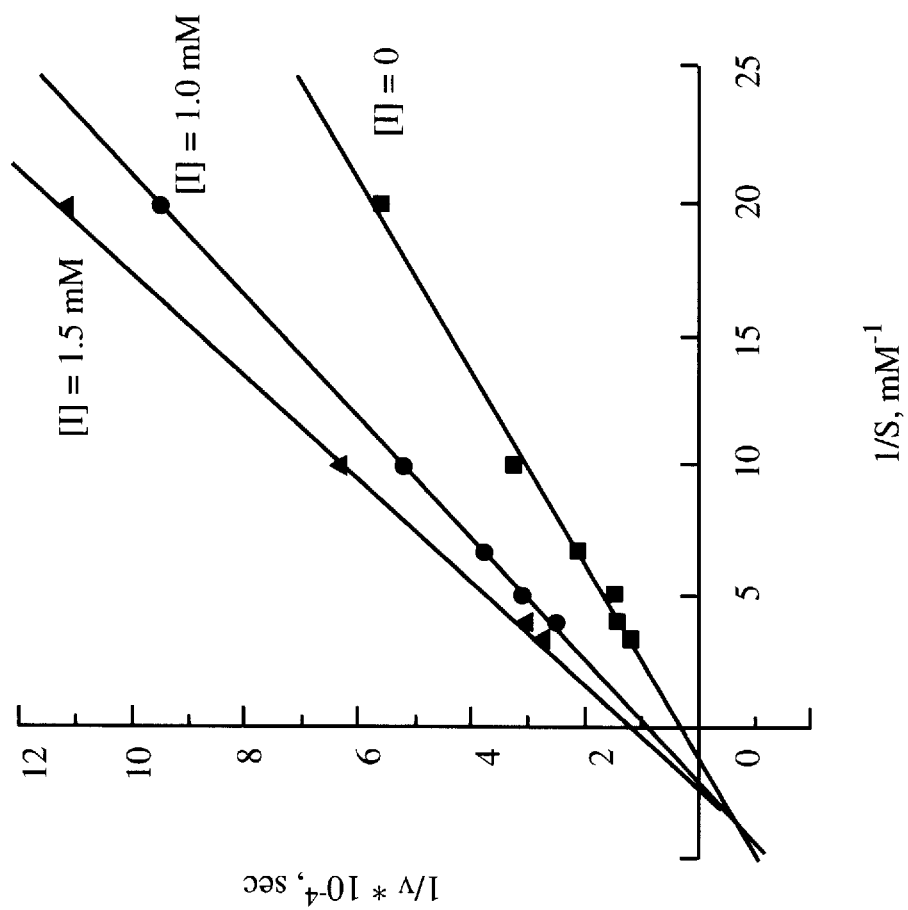
FIG. 4 is a Lineweaver-Burk plot for paraoxon-mediated inhibition of alkaline phosphatase.

In the first set of experiments, the reactions were conducted by varying the CSPD concentration (0.05 to 0.3 mM) in the reaction mixture. In the second set of experiments, CSPD concentration was varied again in the same range, but in the presence of 1.0 mM paraoxon. The third set of experiments was a repeat of the second set, but in the presence of 1.5 mM paraoxon. The concentration of the enzyme was 125 pM in all reaction mixtures in kinetic studies. A Lineweaver-Burk plot was prepared for these three sets of data as shown in FIG. 4, where [I] is the inhibitor concentration.

Figure 5:
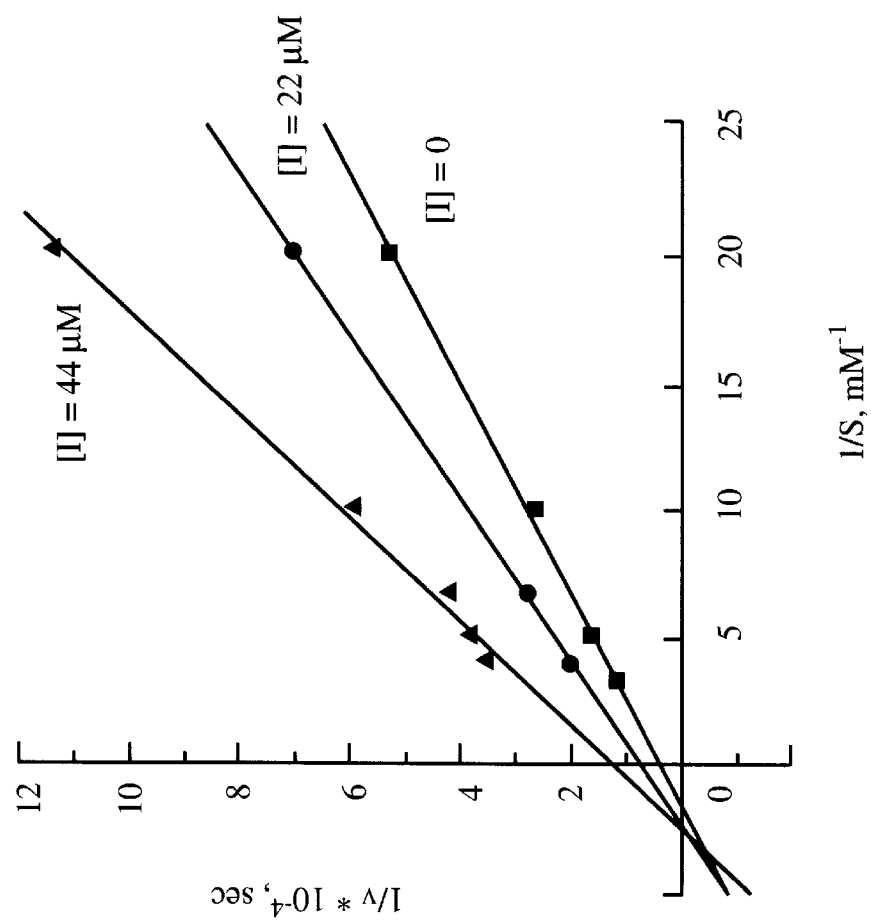
FIG. 5 is a Lineweaver-Burk plot for methyl parathion-mediated inhibition alkaline phosphatase.
Figure 6:
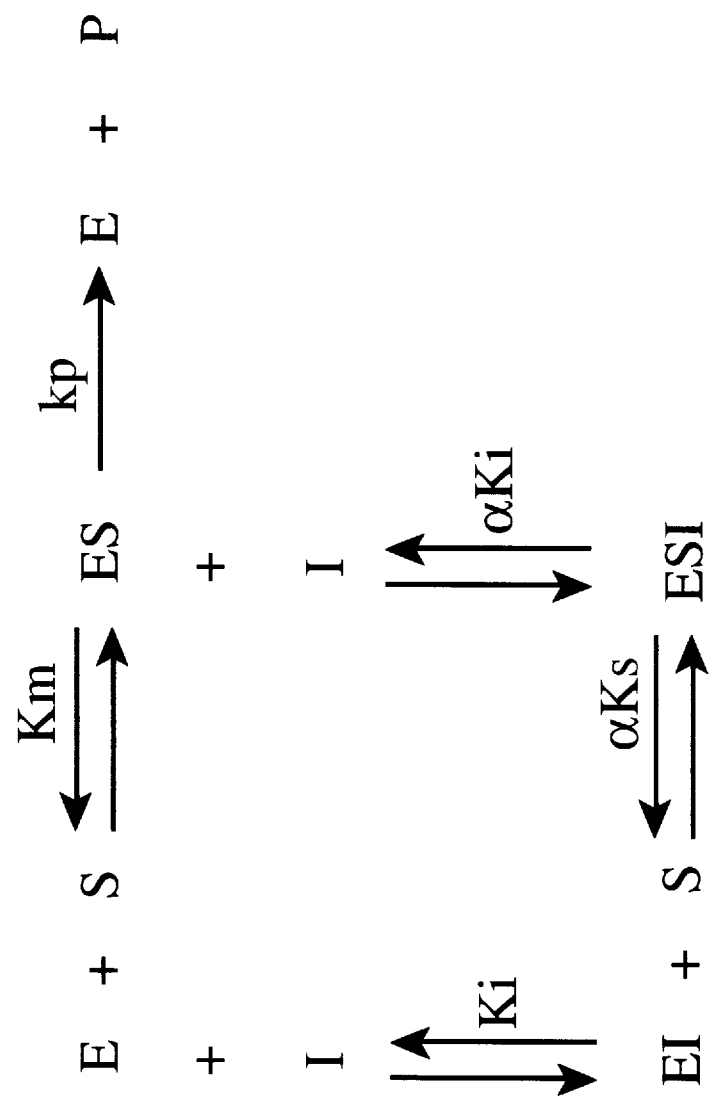
FIG. 6 is a generalized schematic diagram of the enzyme inhibition of the reaction of FIG. 1 caused by the inhibitor compound being detected by the method of this invention.

Typically, the lines in a Lineweaver-Burk plot meet either on the x-axis or on the y-axis, for non-competitive and competitive inhibition, respectively. However, it is interesting to note that the lines do not intersect on either of the axes in the present case (FIG. 4). This behavior suggests a mixed type of inhibition in which the inhibitor not only binds to the enzyme, but affects the association of the substrate with the enzyme. Another OP-based pesticide, methyl parathion, also exhibited a similar behavior. The results of these experiments are shown in FIG. 5. The scheme in FIG. 6 illustrates the mixed inhibition of the enzyme by the pesticide, where "E" is the enzyme, "S" is the substrate (CSPD), and "P" the product of the reaction. ES is the enzyme-substrate complex, I is the inhibitor, EI is the enzyme-inhibitor complex, ESI is the enzyme-substrate-inhibitor complex, $K_m$ and $K_i$ are equilibrium constants, and $\alpha$ is the interaction parameter that is a measure of inactivation of the enzyme in the presence of the inhibitor.

Figure 7:
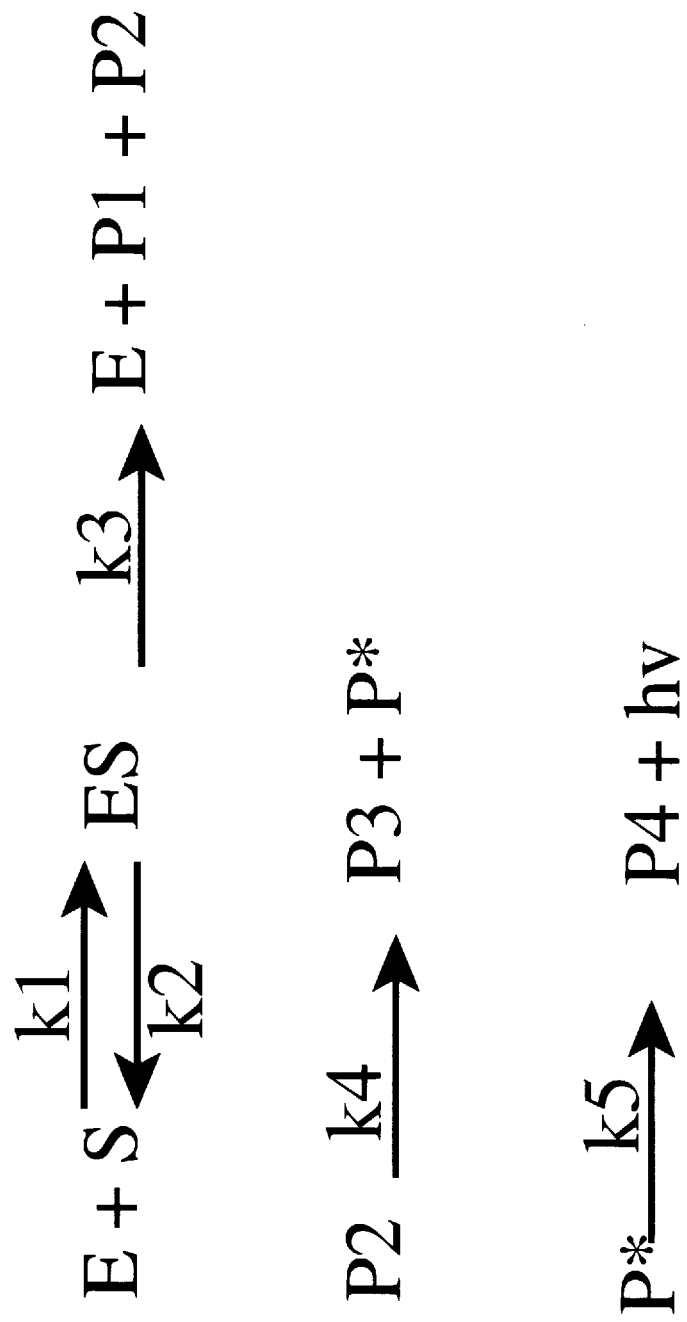
FIG. 7 is a schematic diagram of the kinetics of the reaction scheme of FIG. 6.

FIG. 7 portrays the same reaction as FIG. 6, but represented by three equations written to derive a kinetic expression. The terms in the equation are defined as follows. E is the enzyme, S is the substrate, ES is the enzyme-substrate complex, P1, P2, P3 and P4 are products numbers 1, 2, 3, and 4, respectively, P* is the unstable intermediate product, k1, k2, k3, k4 and k5 are reaction rate constants, and hv is the light energy released in the reaction. The kinetic constants, calculated from the slopes and intercepts of the curves of FIGS. 4 and 5, are given in Table I.

TABLE I

| Inhibitor | Vmax (Sec$^{-1}$) | Km (mM$^{-1}$) | $K_i$ (mM) | $\alpha$ |
|---|---|---|---|---|
| None | $3 \times 10^4$ | 0.81 | — | — |
| Paraoxon | — | — | 1.7 | 0.334 |
| Methyl parathion | — | — | 0.06 | 0.380 |

Kinetic parameters for paraoxon and methyl parathion inhibition

Detection and Quantification of Pesticides

The extent of inhibition of alkaline phosphatase activity by a range of pesticide concentrations was studied at a fixed CSPD concentration. A stock solution of paraoxon or methyl parathion of a known concentration was prepared. As before, the reaction mixture was prepared by mixing predetermined volumes of CSPD, pesticide and enzyme solutions. The concentrations of CSPD and the enzyme were fixed, and the pesticide concentration was varied either by adding a given volume of diluted pesticide solutions or by adding different volumes of the concentrated stock pesticide solution and making up the reaction mixture volume with buffer. In all cases, the reaction was initiated by adding the enzyme solution just before the data collection, which was continued well past the linear portion of the count rate-versus-time curve. The initial slopes of these curves (in their linear portions) are proportional to the enzyme activity. Unlike the treatment in kinetics, the enzyme activity here is expressed directly as slopes of count rate-versus-time curves for simplicity. This sequence of steps was carried out at each successively lower pesticide concentration until the detection limit was reached. In practice, the data points required for computing slopes could be collected within the first 10 to 20 seconds.

During the course of establishing detection limits, the difference in the initial slopes for a sufficiently low concentration of pesticide and the corresponding control (without pesticide) disappeared when the molar ratio of CSPD to the pesticide approached a value in the range of 1–2. See Table II.

TABLE II

| [CPSD] ($\mu$M) | Paraoxon detection limit (ppm) | [CSPD]/[Paraoxon] in reaction mixture |
|---|---|---|
| 290 | 50 | 1.6 |
| 1.82 | 0.4 | 1.3 |
| 0.874 | 0.11 | 2.2 |
| 0.290 | 0.05 | 1.6 |

Paraoxon detection limit versus molar ratio of CSPD to paraoxon

For example, at a concentration of 1.82 $\mu$M CSPD, 364 $\mu$M (100 ppm) paraoxon that was sufficient to completely inhibit the enzyme activity, the molar ratio of CSPD to paraoxon would be $5\times10^{-3}$. The corresponding slope of the count rate-versus-time curve would be negligible or very small compared to that of the control. As the pesticide concentration was reduced from 100 ppm at constant CSPD and enzyme concentrations, the molar ratio and the curve initial slope would increase and approach the control value. As the ratio approached the above range, the difference between the initial slopes of the curves for pesticide and the control would diminish, and the detection limit with respect to that particular CSPD concentration used would have been reached (0.4 ppm in this example, see Table II). In this example, above a ratio of 1.26 between CSPD and the pesticide, the enzyme inhibition due to the pesticide was negligible.

Figure 8:
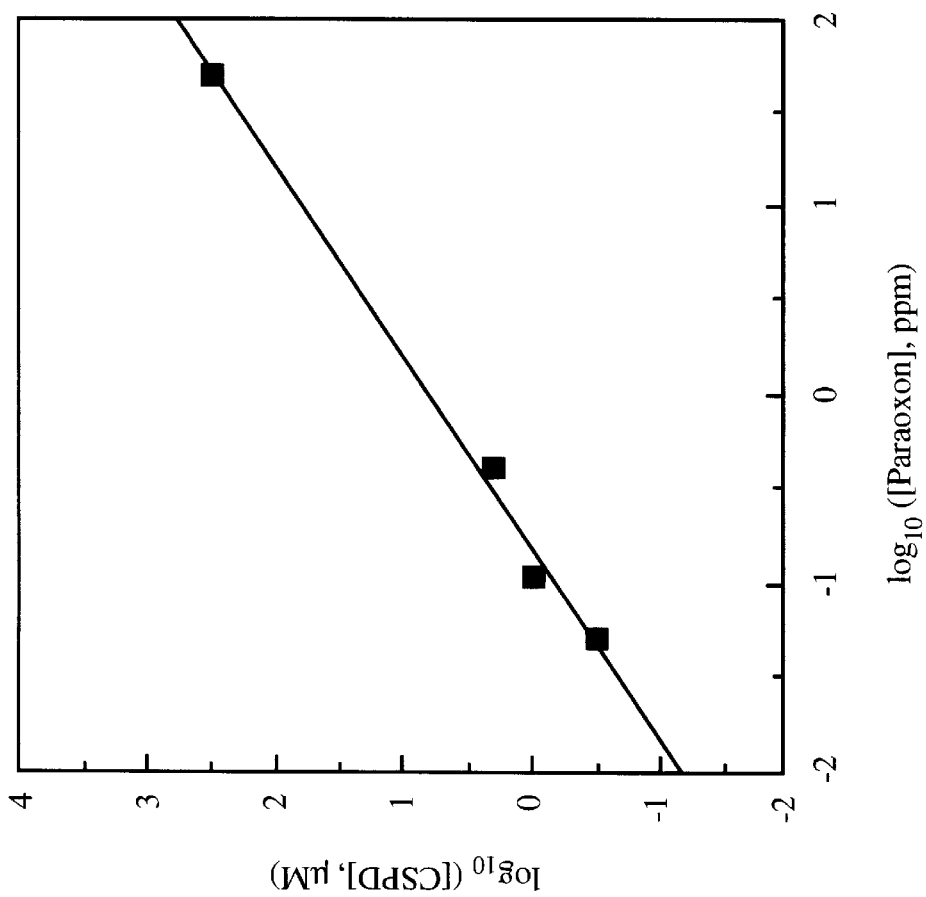
FIG. 8 is a plot of the CSPD-dependent detection limit of paraoxon.

FIG. 8 illustrates the dependence of the lowest detectable concentration of paraoxon on CSPD concentration. In principle, any concentration of paraoxon could be detected in solution, provided the concentration of CSPD would not exceed the corresponding value from the plot. Thus, the CSPD concentration range could be adjusted in a dynamic fashion to detect any concentration of a given OP-based pesticide. The above relation could be used to advantage in developing an automated process for the remote detection of toxic compounds present in unknown quantities. The amount of CSPD could be adjusted by a feedback controller which compares the inhibited chemiluminescence signal to the corresponding control signal.

The data presented in FIG. 8 clearly indicates that the detection limit of paraoxon could be further lowered by reducing the CSPD concentration, but only at the cost of the instrument signal to noise ratio (S/N) and the intensity of photon emission. Without significant sacrifice of S/N ratio, it was found that the CSPD concentration could be reduced in the reaction mixture to 0.29 $\mu$M, to enable the detection of 50 ppb paraoxon and about 80 ppb of methyl parathion. By enhancing the efficiency of collection optics, lower CSPD concentrations could be used that would permit sub-ppb level detection.

Figure 9:
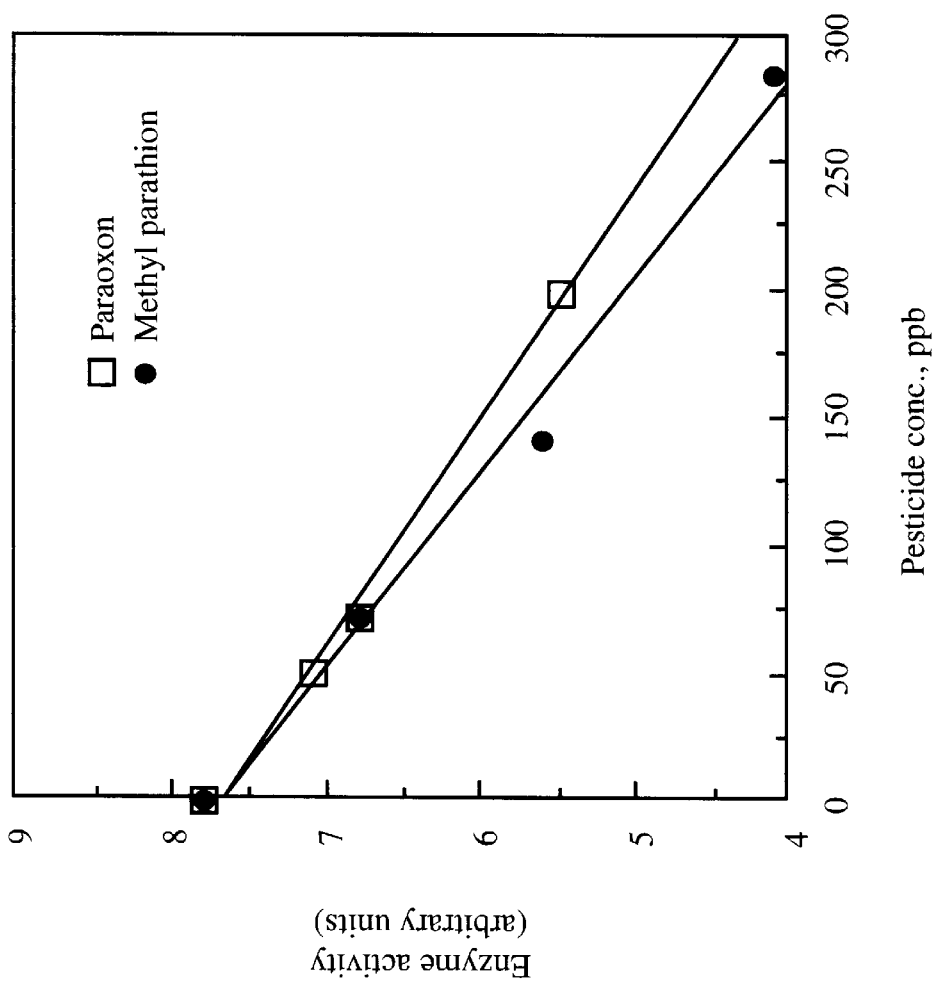
FIG. 9 is a plot of calibration curves for paraoxon and methyl parathion inhibition.

FIG. 9 illustrates the calibration curves for both paraoxon and methyl parathion. Other OP-based pesticides that showed a similar behavior, (data not shown) were malathion and Diazinon. Malathion was not particularly stable at the working pH of 10. Spontaneous hydrolysis was observed at this pH, as has been reported. This problem could be overcome by conducting the reactions at a lower pH and using acid phosphatase as the enzyme. Thus, it can be generalized that the chemiluminescence technique could be used to detect ppb levels of various organophosphorus based compounds, including, but not limited to, pesticides and nerve agents.

The described technique can be used to develop fiber-optic biosensors for the remote detection of pesticides. For example, alkaline phosphatase could be immobilized on an optical fiber and the chemiluminescence signal generated on the fiber surface could be transduced via fiber to the detector.

Figure 10:
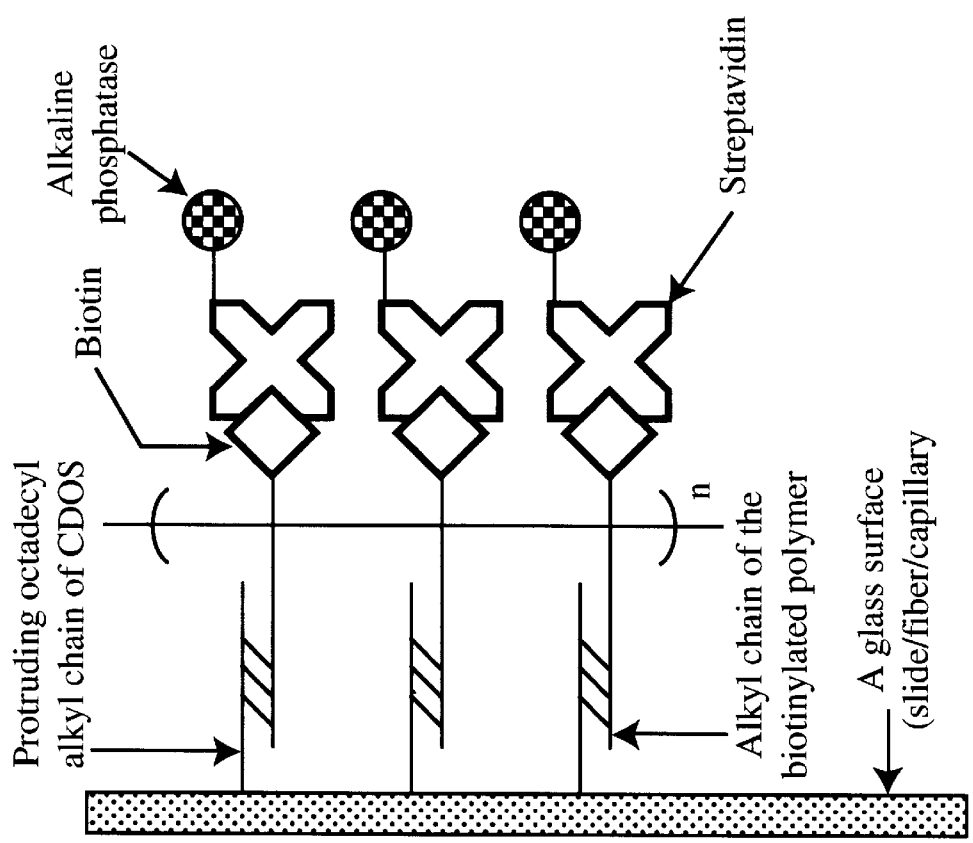
FIG. 10 is a schematic diagram of one methodology of immobilizing the enzyme.

FIG. 10 is a schematic illustration of one of the three different methodologies studied to immobilize enzymes on a glass surface. A biotinylated thiophene copolymer bound to the silanized glass surface by the alkyl chains serves as a rugged support as well as a source for multiple attachment sites for streptavidin conjugated enzymes. The conducting nature of the polymer may play a role in signal transduction. These methodologies have been shown to be successful in conjunction with optical fibers and glass capillaries. Another approach would be to grow a brush-like polymer on the glass surface and functionalize the conjugated polymer with biotin moieties for subsequent streptavidin conjugated protein binding. The third approach is a control in which the biomolecule is covalently attached to the glass surface.

Metal Ion Detection

Trace analysis of heavy metals is important for chemical, environmental and biomedical fields. Chemical and biochemical methods using optical or electrochemical techniques of signal transduction to detect metals have been studied. Biochemical means of detection of metal ions often involve metalloenzymes, which require metals as cofactors for their enzyme activity.

Alkaline phosphatase (EC 3.1.3.1), a non-specific phosphomonoesterase, is a dimeric metalloenzyme containing four zinc ions and two magnesium ions coordinated to the active site. Although Zn(II) ion is necessary for enzyme activity, excessive amounts of the ion results in inhibition of enzyme catalytic activity. Moreover, some other metal ions, such as Be(II) and Bi(III), are also known to be potent inhibitors of alkaline phosphatase. Removal of metal ions from native enzyme with strong chelating agents or by partial denaturation of the enzyme results in the formation of the corresponding apoenzyme that lacks catalytic activity. By exposure to a Zn(II) ion-containing solution, the apoenzyme can be reversibly activated. The restored enzyme activity is proportional to the stoichiometric amount of Zn(II) ion present in the solution, and this measure of activity allows the evaluation of the metal ion content. It is thus possible to develop sensitive methods for the determination of Zn(II) (in stoichiometric excess), Be and Bi based on enzyme inhibition. The presence of Zn(II) can also be determined by the apoenzyme reactivation.

Zn ions in trace levels (ppb range by enzyme reactivation and ppb to ppm range by enzyme inhibition) in bulk solutions have been detected. In addition to Zn, Be and Bi were also determined quantitatively. The technique involved measurement of the chemiluminescence signal generated by the alkaline phosphatase-catalyzed dephosphorylation of chloro 3-(4-methoxy spiro [1,2-dioxetane-3-2'-trichloro-[3.3.1.1]-decan]-4-yl) phenyl phosphate (CSPD), in the presence and absence of metal ions. As described earlier, the assembly and alignment of optical components for the detection system were simple because of in situ light generation in the reaction mixture.

Figure 11:
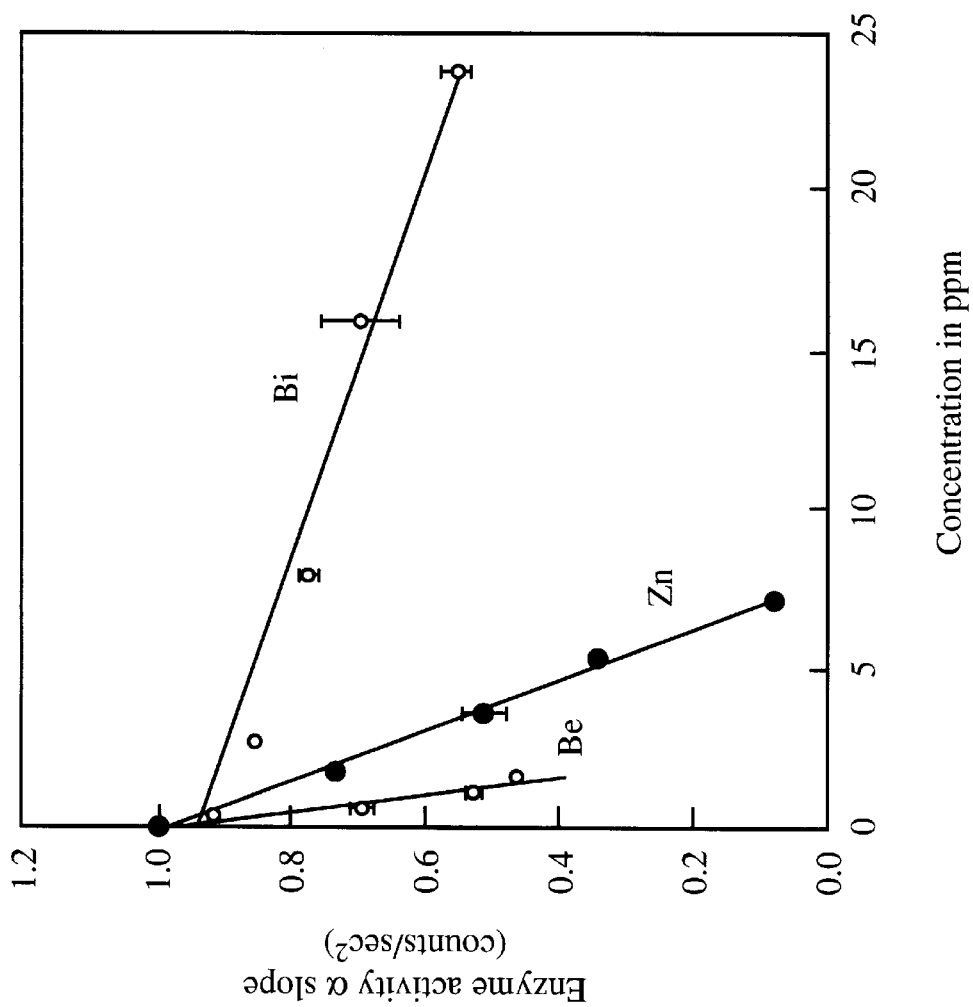
FIG. 11 is a group of calibration curves showing alkaline phosphatase inhibition by ions of Be, Zn and Bi in bulk solutions.
Figure 12:
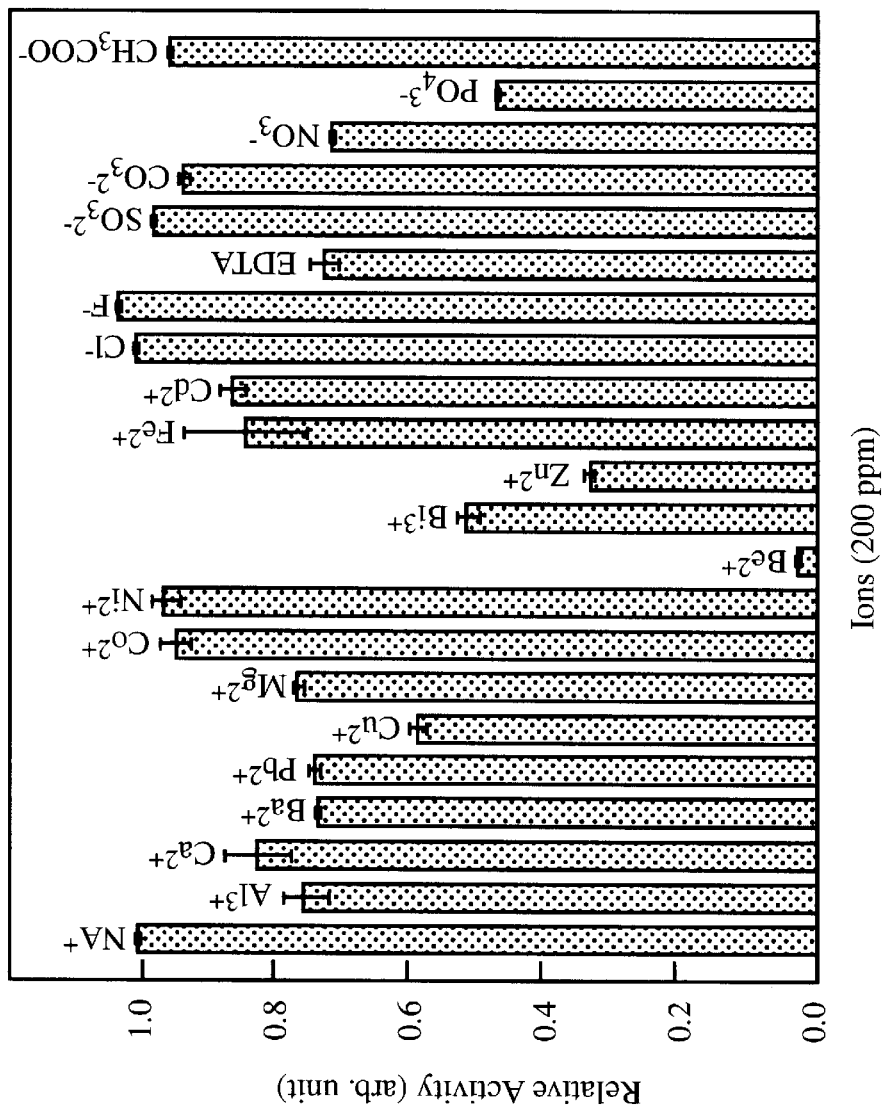
FIG. 12 is a graph of the effect of potentially interfering ions on the enzyme activity in metal ion determination.

FIG. 11 illustrates the detection levels and inhibition of the enzyme activity by Zn, Be, and Bi in bulk solutions. By inhibition, the detection limits for Zn, Be and Bi are 170 ppb, 1 ppb, and 1.8 ppm, respectively. FIG. 12 illustrates the effect of various potentially interfering ions on the enzyme activity. The enzyme activity was measured in the presence of 200 ppm of each ion. Clearly, Be is the most interfering ion. A method to mask the effect of Be while measuring the amount of other ions is presented later in the text.

Figure 13A:
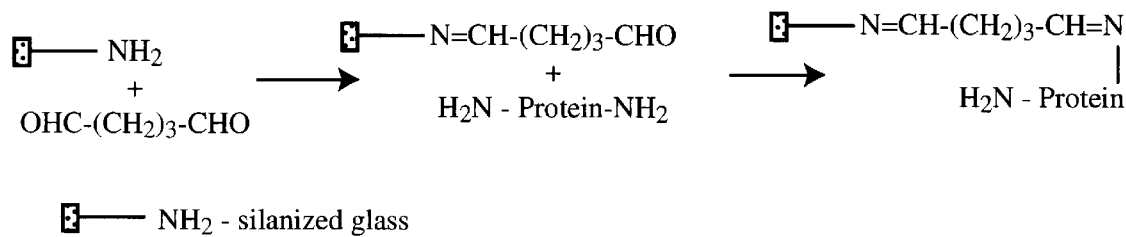
FIG. 13A is a reaction scheme for an alternative method of immobilizing the enzyme for use in the methods of this invention.
Figure 13B:
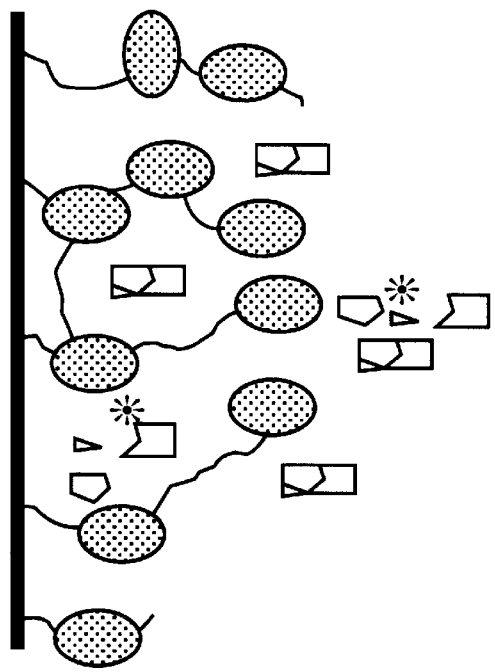
FIG. 13B is a schematic representation of the enzyme immobilization in FIG. 13A.

Activity measurements were also made with immobilized alkaline phosphatase immobilized as shown in FIGS. 13A and 13B using a bifunctional reagent, glutaraldehyde. Upon introduction of the substrate solution, light generation was observed on the glass surface (for example, on the inside walls of a glass capillary) due to enzymatic dephosphorylation of CSPD. The strength of the chemiluminescence signal is directly proportional to the enzyme activity at a given chemiluminescence substrate concentration.

The following materials were used in the present study in addition to those described in the earlier section. Tris-HCl, ammonium sulfate (enzyme grade), zinc sulfate, p-nitrophenyl phosphate, 3-aminopropyltriethoxysilane and glass beads (200 mm) were supplied by Sigma Chemical Company (St. Louis, Mo.). Sodium acetate, sodium chloride and magnesium chloride were purchased from Fisher Scientific (Fair Lawn, N.J.). Beryllium sulfate, glutaraldehyde and bismuth nitrate were purchased from Aldrich Chemical Company (Milwaukee, Wis.). All chemicals were of analytical grade and were used as received.

Figure 14:
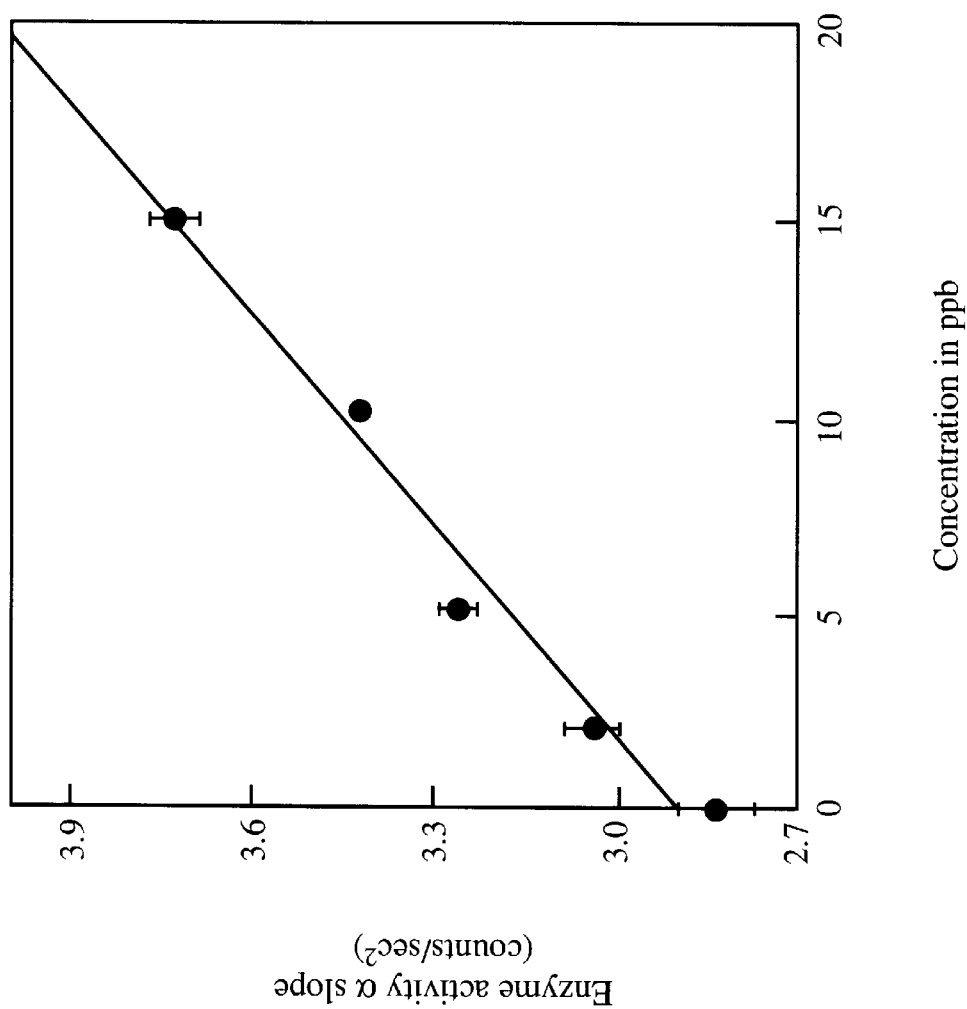
FIG. 14 is a graph of the detection of Zn ions by apoalkaline phosphatase reactivation in solution.

Apo-alkaline phosphatase was prepared by dialyzing the native enzyme (10 mg/ml, in phosphate buffered saline, pH 7.2) against two liters of 2M ammonium sulfate, pH adjusted to 9, at 4° C. for 24 hours with two changes of dialysate. Ammonium sulfate was removed subsequently by dialyzing twice against two liters of a buffer containing 0.01M Tris-HCl, 0.01M sodium acetate, 0.1M sodium chloride and pH adjusted to 9. Prior to CSPD hydrolysis reactions, the native and apoenzyme activities were checked by following the hydrolysis of p-nitrophenyl phosphate (in 0.2M Tris-HCl buffer, pH 8). The initial rate of formation of p-nitrophenol was recorded at 405 nm using a Perkin-Elmer Lambda 9 spectrophotometer. Zinc ion concentrations in the native and apoenzyme were checked by Direct Current Plasma (DCP) spectometery (model SMI III Spectrametrics, Inc.). Stock solutions of Zn(II) and other metals were prepared by dissolving appropriate amounts of spectral grade salts in distilled dionized water. Further dilutions were made in assay buffer containing 0.1M diethylamine (DEA) and 1 mM $MgCl_2$ at pH 10. FIG. 14 shows the activity regeneration of apoalkaline phosphatase in the presence of different concentrations of Zn solutions. Thus, the curve in FIG. 14 serves as calibration for Zn ion quantification by apoenzyme activity regeneration.

Glass beads and the inner surfaces of test tubes and 100 $\mu$l glass capillaries were silanized by treatment with 10% aqueous 3-aminopropyltriethoxysilane, pH 3.5, at 75° C. for 3 hours. After silanization, the surfaces were washed with distilled water and dried at 100° C. overnight. Dry silanized glass was activated by soaking it in a 1% glutaraldehyde solution at 4° C. for 2 hours followed by washing with distilled water. Moist activated glass was treated with alkaline phosphatase at 4° C. for 1.5 hours. The resulting immobilized alkaline phosphatase preparation was then washed with distilled water and phosphate buffer after reducing the methane groups (formed during the coupling of aldehyde group with enzyme amino group) by incubating the enzyme-glass conjugate for two minutes in the immobilization supernatant containing 200 mg $NaBH_4$. Repeated alternate treatment of the silanized glass with glutaraldehyde and alkaline phosphatase can help build a multilayer of enzyme on the glass surfaces. In the present study, alkaline phosphatase was used as illustrated in FIGS. 11A and 11B. The immobilized enzyme was stored at 4° C. in assay buffer. A packed bed of glass beads with covalently immobilized enzyme was also prepared in a simple pasteur pipet in preliminary attempts to develop a continuous flow cell. The immobilized enzyme on beads retained its activity well over six months time when stored in assay buffer at 4° C.

Substrate solution was prepared by adding the supplied 25 mM CSPD solution to a 10% solution of enhancer in assay buffer for a final CSPD concentration of 0.4 mM. The stock solutions, stored at 4° C., were brought to room temperature prior to the reaction. The reaction mixture was prepared separately by adding the assay buffer to predetermined volumes of CSPD and metal ion solution to make up the final volume. The reaction was initiated by adding 0.5 ml of this solution to a glass test tube, or a 100 $\mu$l capillary containing the immobilized enzyme.

For the detection of Zn, Be and Bi ions by enzyme inhibition, the reaction mixture was prepared by mixing 0.25 ml of 0.4 mM CSPD solution (10% enhancer) and 0.125 ml of metal ion solutions at different concentrations. The volume was brought to 0.5 ml with buffer. Reaction was initiated by placing this mixture in a test tube in which alkaline phosphatase was immobilized. Zn ion detection by reactivation of the apoenzyme was carried out with by first incubating 0.5 ml of metal ion solution in a test tube with immobilized apoenzyme for 2 minutes. To this, 1 ml of buffer and 0.5 ml of 0.4 mM CSPD solution were added to initiate the reaction. Signal collection was as described earlier. The data has been normalized to the control (i.e., no inhibition) results.

A typical chemiluminescence signal profile from the CSPD hydrolysis is shown in FIG. 12A for two cases: (a) in the absence, and (b) in the presence of a metal ion (zinc) in solution. FIG. 12B gives the same profile for the enzyme in the immobilized state. As explained earlier, the initial slope of these profiles was used to measure the reaction rate.

Immobilized alkaline phosphatase shows similar chemiluminescence signal profile to that in bulk solution under similar experimental conditions. However, the signal intensity with immobilized enzyme is weaker perhaps due to relatively fewer numbers of enzyme molecules (calculated on the basis of complete surface coverage by the immobilized enzyme) catalyzing the reaction. It is also possible that the enzyme may have been partially inactivated during the immobilization process. In order to enhance the initial rate of reaction, the amount of enzyme on the glass surface could be increased by repeated alternate treatment of the surface with glutaraldehyde and the enzyme.

Detection of Zn, Be, Bi Ions by Inhibition of Immobilized Alkaline Phosphatase

Figure 15B:
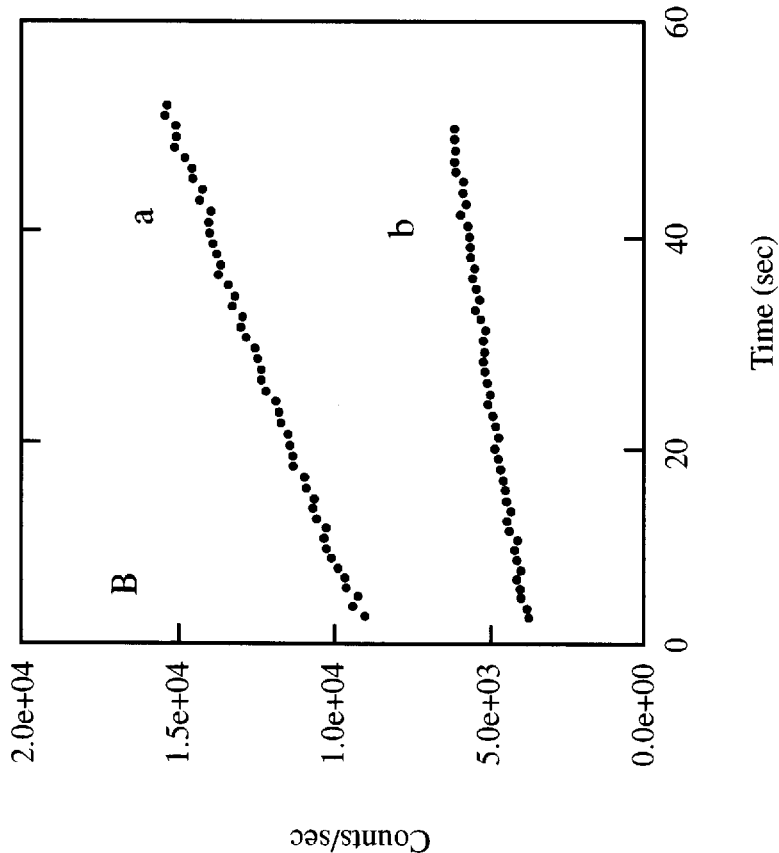
FIG. 15B is a similar profile for a higher concentration of zinc and with the enzyme immobilized on the inside walls of a capillary tube.
Figure 15A:
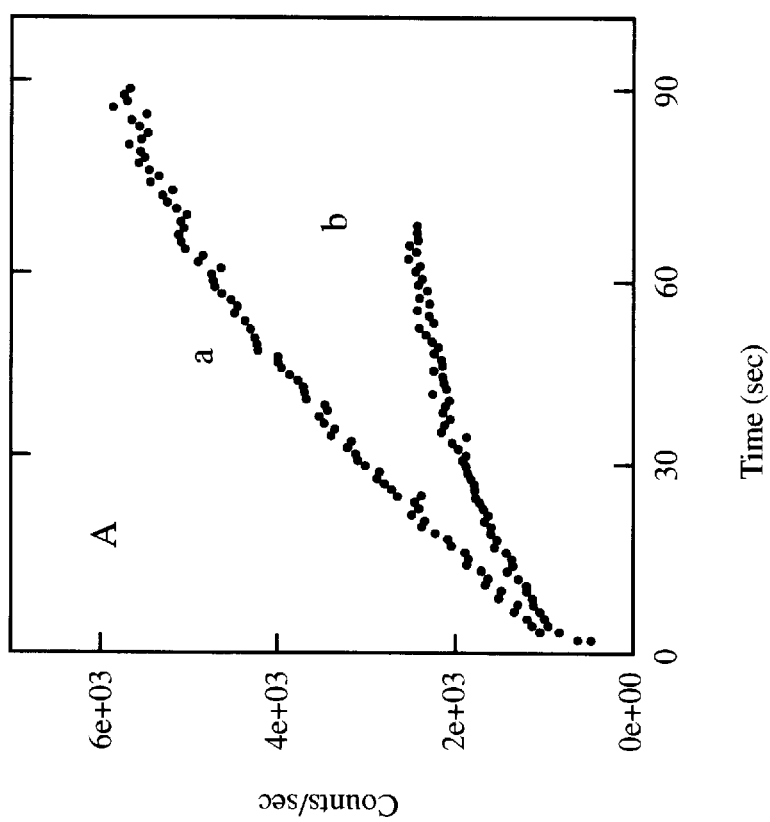
FIG. 15A is a chemiluminescence profile of the alkaline phosphatase-catalyzed dephosphorylation of CSPD in the absence and in the presence of zinc in solution.
Figure 16A:
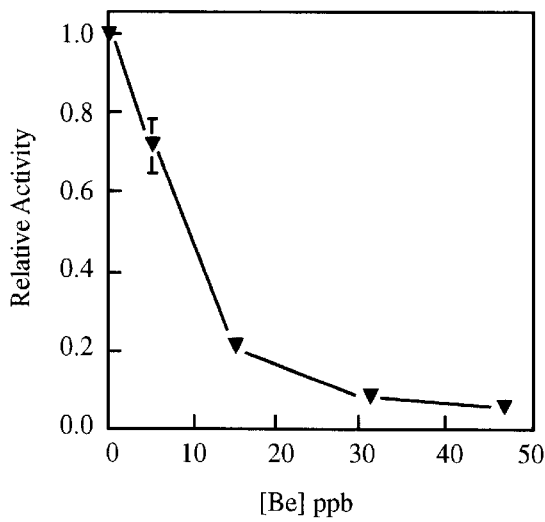
FIGS. 16A through 16C are graphs of the relative enzyme activity of immobilized alkaline phosphatase in the presence of inhibiting metal ions Be, Zn and Bi, respectively, in relation to the activity in the absence of those metal ions.
Figure 16B:
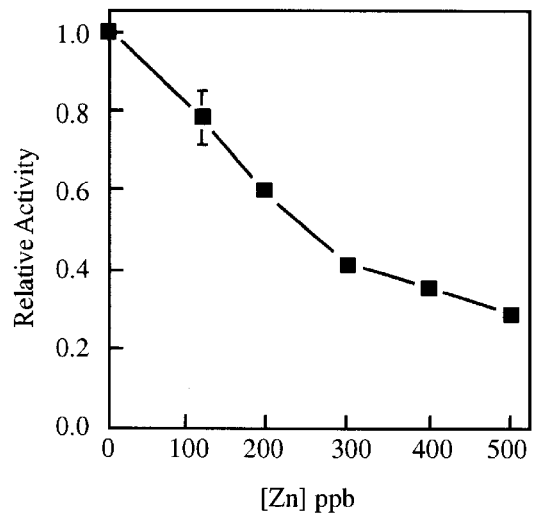
Figure 16C:
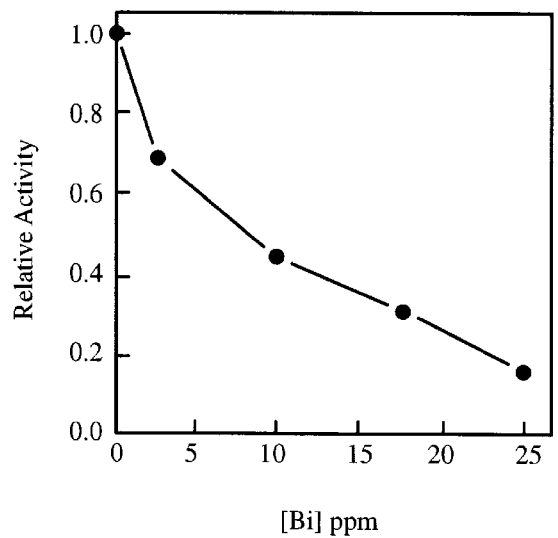

Inhibition of alkaline phosphatase in the presence of Zn(II), Be and Bi can be used to quantify the metal ion concentrations. As described earlier, the enzyme was immobilized on the inside walls of a test tube. Data collection for successive lower metal concentrations was continued until the detection limit was reached, the point where the difference in the initial slopes for the lowest metal ion concentration and the corresponding control (absence of any metal ion inhibitor) is indistinguishable. The error bars in FIGS. 16A through 16C signify the standard deviation for three different samples taken for the same metal ion concentration. FIGS. 15A, 15B and 15C illustrate the calibration curves obtained for Be, Zn and Bi ions, respectively. Detection of 5 ppb Be, 120 ppb Zn and 2.4 ppm Bi was achieved with immobilized alkaline phosphatase. These detection limits are comparable to values reported in the literature. Detection of these three metal ions can be made more specific by using different masking agents and by sample pre-treatment.

Figure 17:
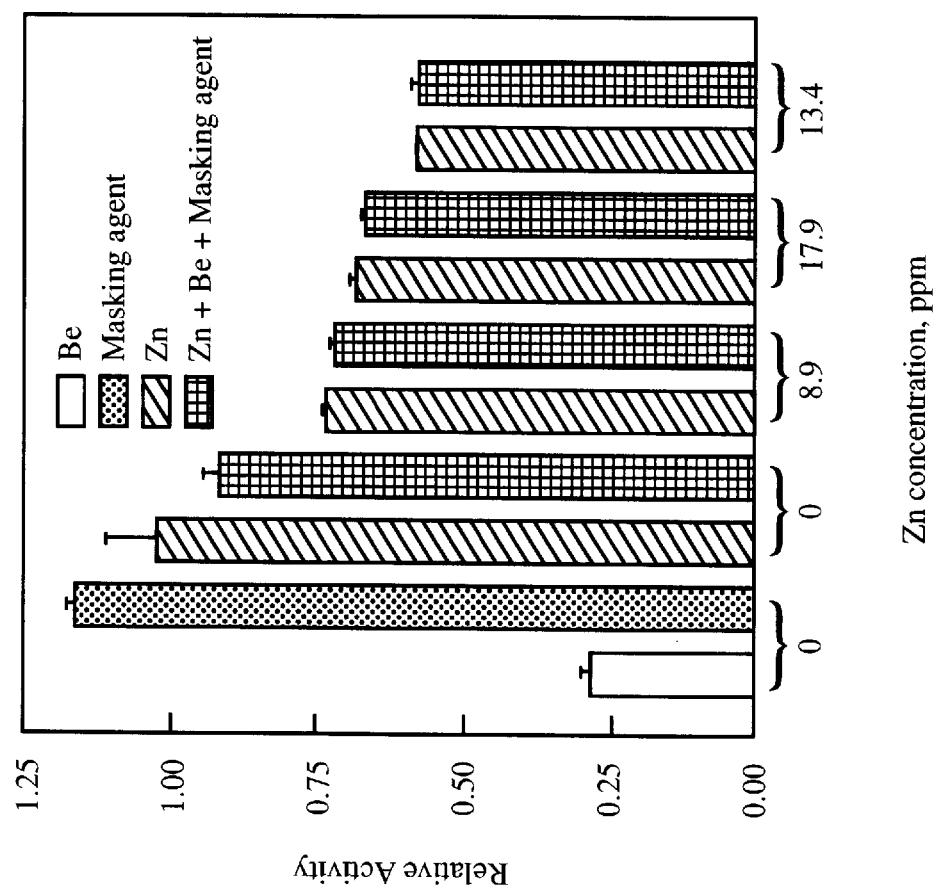
FIG. 17 is a graph of the determination of Zn ions in the presence of Be when Be is masked by acetylacetone and NaF.

For example, Zn ions can be determined in the presence of Be by selectively masking Be with acetylacetone and sodium fluoride. Acetylacetone masks the effect of Ag, Ni, Co, Cu and Be, while sodium fluoride masks the effect of Al, Ca, St and Mn. FIG. 17 shows how Zn ions can be detected at various concentrations in the presence of Be. The reaction mixture was prepared by mixing 0.25 ml of 5 $\mu$M CSPD solution, 0.125 ml of metal ion solution, 0.125 ml of the masking agent solution containing 0.02% v/v of acetylacetone in 0.1M NaF and 0.2 ml of enzyme solution. Controls were prepared by replacing the metal ion solution or masking agent with assay buffer.

Detection of Zn Ion by Reactivation of Immobilized Apo-Alkaline Phosphatases

Figure 18:
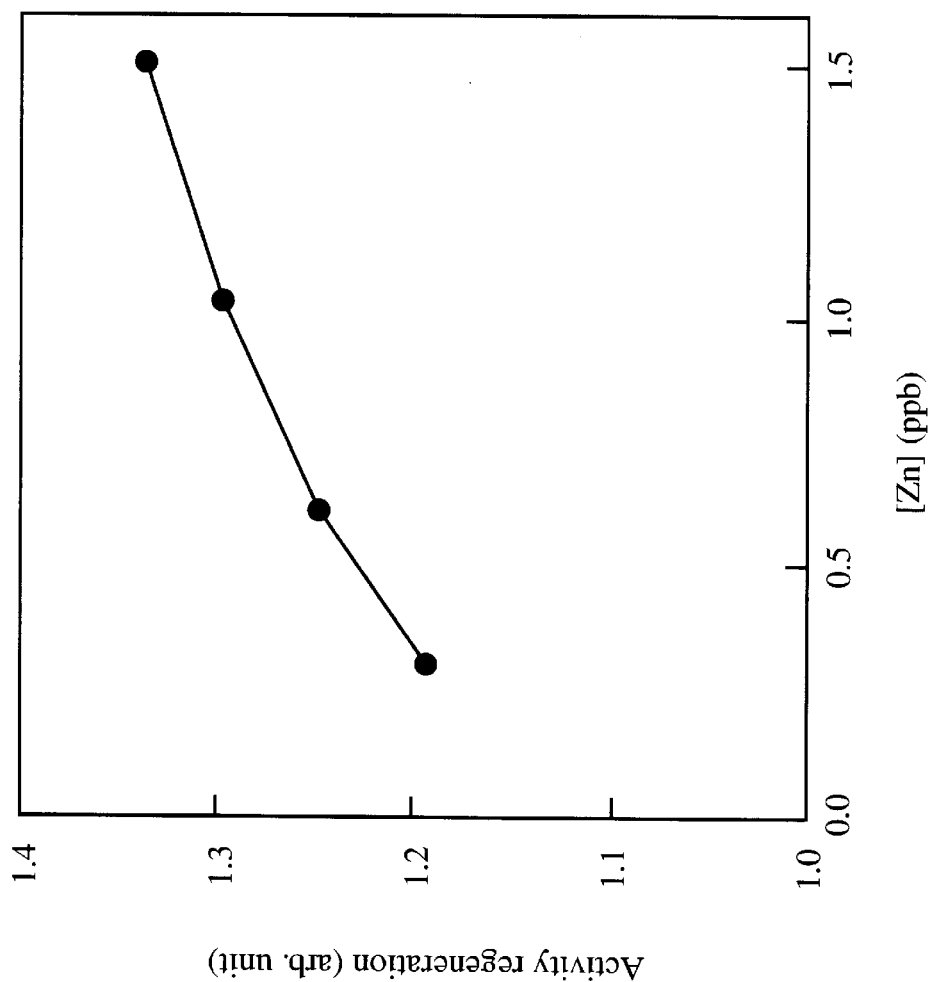
FIG. 18 is a graph of the relative enzyme activity of the apoalkaline phosphatase enzyme as a function of zinc ion concentration in solution in comparison to that of the apoenzyme in the absence of the metal ions.

Apo-alkaline phosphatase exhibits reduced catalytic activity towards CSPD as compared to the undialyzed native enzyme. The activity can be regenerated by adding Zn(II) ions in stoichiometric amounts. This fact was used to develop a sensitive chemiluminescence technique for the determination of Zn(II) ions using immobilized apo-alkaline phosphatase. FIG. 18 shows the calibration curve for Zn(II) ions by the regeneration of immobilized apo-alkaline phosphatase. A detection limit of 0.3 ppb was achieved.

To develop optical fiber-based biosensor applications for metal ion detection, the native enzyme was immobilized on the inner surface of a 100 $\mu$l glass capillary. With identical analyte and CSPD concentrations, these three metal ions can be detected to the same extent as in a test tube. Zn(II) was detected by both inhibition and activity generation methods.

Preliminary studies of enzyme immobilization on glass beads to develop a continuous flow cell were conducted. The glass beads with immobilized enzyme were subjected to 0.4 mM CSPD at a flow rate of 0.75 ml/min. This method yielded a signal two orders of magnitude stronger than that observed for test tube-based immobilization.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A method of detecting the presence of an organophosphorus compound in a liquid medium consisting of:

providing a 1,2-dioxetane phenyl phosphate compound said compound being a chloro3-(4-methoxy spiro [1,2-dioxetane-3-2'-trichloro-[3.3.1.1]-decan]-4-yl) phenyl phosphate;

providing an enzyme that catalytically degrades said 1,2-dioxetane phenyl phosphate compound to produce light, the catalytic activity of said phosphates being inhibited by organophosphorus compounds;

exposing said 1,2-dioxetane phenyl phosphate compound and said phosphatase together to a medium which may contain an organophosphorus compound;

monitoring the light produced by chemiluminescence after the exposing step; and determining, from the monitored light, the presence in the medium of the organophosphorus compound.

2. The method of claim 1 in which said enzyme is a phosphatase.

3. The method of claim 2 in which said phosphatase is alkaline phosphatase.

4. The method of claim 2 in which said phosphatase is acetylcholine esterase.

5. The method of claim 2 in which said phosphatase is phosphodiesterase.

6. The method of claim 2 in which said phosphatase is acid phosphatase.

7. The method of claim 2 in which said phosphatase is phosphotriesterase.

8. The method of claim 1 in which said enzyme is an enzyme which catalyzes the hydrolysis of phosphate bond in said 1,2-dioxetane phenyl phosphate compound.

9. The method of claim 1 in which said organophosphorus compound is an organophosphorus nerve agent.

10. The method of claim 9 in which said organophosphorus compound is selected from the group of nerve agents consisting of Soman, Sarin, Tabun and VX.

11. The method of claim 1 in which said organophosphorus compound is an organophosphorus pesticide.

12. The method of claim 11 in which said organophosphorus compound is selected from the group of pesticides consisting of malathion, methyl parathion, parathion and paraoxon.

13. The method of claim 1 in which the step of providing an enzyme includes binding said enzyme to a substrate.

14. The method of claim 13 in which the step of binding said enzyme to a substrate includes attaching Streptavidin-conjugated enzyme to a biotinylated compound which is fixed to a substrate.

15. The method of claim 14 in which said biotinylated compound is covalently linked to a conductive polymer substrate.

16. The method of claim 13 in which the step of binding said enzyme to a substrate includes immobilizing said enzyme using hydrophobic interactions with glutaraldehyde cross-linking.

17. The method of claim 13 in which said substrate is a fiber optic fiber for remote detection.

18. The method of claim 1 further including the step of resolving, from the monitored light, the concentration in the medium of the organophosphorus compound.

19. The method of claim 18 in which the step of resolving the organophosphorus compound concentration includes exposing said 1,2-dioxetane phenyl phosphate compound and said enzyme together, without the presence of an organophosphorus compound, and measuring the resulting light production, and then comparing said monitored light to said measured resulting light production.

20. A method of quantifying a species selected from one of the groups consisting of organophosphorus compounds and metal ions which may be present in a liquid medium being monitored for the presence of a said species, consisting of:

providing a phenyl-substituted 1,2-dioxetane compound, said compound being a chloro 3-(4-methoxy spiro [1,2-dioxetane-3-2'-trichloro-[3.3.1.1]-decan]-4-yl) phenyl phosphate, that is catalytically degradable to produce light;

providing an enzyme which catalytically degrades said compound to produce light, and whose catalytic activity toward said compound is inhibited by the species being quantified;

exposing said compound and said enzyme together to the medium being monitored for the species being quantified; and resolving from the light produced after the exposing step, the concentration in the medium of the species being quantified.

21. A method of detecting the presence of a substance selected from one of the groups consisting of organophosphorus compounds and metal ions being monitored in a liquid medium which may contain a substance being monitored, consisting of:

providing a 1,2-dioxetane phenyl phosphate compound, said compound being a chloro 3-(4-methoxy spiro [1,2-dioxetane-3-2'-trichloro-[3.3.1.1]-decan]-4-yl) phenyl phosphate;

providing a phosphatase that catalytically degrades said 1,2-dioxetane phenyl phosphate to produce light, wherein the catalytic activity of the phosphatase toward the 1,2-dioxetane phenyl phosphate compound is altered by the presence of the substance being monitored;

exposing said 1,2-dioxetane phenyl phosphate compound and said phosphatase together to the medium which may contain the substance being monitored;

detecting light produced after the exposing step; and determining, from the detected light, the presence in the medium of the substance being monitored.

22. The method of claim 21 in which the substance of said group consisting of metal ions being monitored is further selected from the group consisting of Zn, Be and Bi.

23. The method of claim 21 in which the determining step includes resolving a decrease in light production caused by phosphatase activity inhibition by the substance being monitored.

24. The method of claim 21 wherein the substance being monitored includes a metal present in said phosphatase, the method further including the step of removing at least some of said metal from said phosphatase to create an apoenzyme before the exposing step, wherein said substance being monitored regenerates said apoenzyme to increases catalytic activity.

25. The method of claim 24 in which said metal is zinc.

26. The method of claim 21 further including the step of providing a masking agent for a second substance that also alters the catalytic activity of phosphatase toward said 1,2-dioxetane phenyl phosphate compound, said masking agent provided before the exposing step to allow detection of said substance being monitored.

27. The method of claim 21 further including the step of resolving, from the detected light, the concentration in the medium of the substance being monitored.

* * * * *